(12) United States Patent
Boone et al.

(10) Patent No.: US 6,261,820 B1
(45) Date of Patent: *Jul. 17, 2001

(54) FIBRONOLYTICALLY ACTIVE POLYPEPTIDE

(75) Inventors: Thomas C. Boone; Huimin Li, both of Newbury Park; Michael B. Mann, Thousand Oaks, all of CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/411,329

(22) Filed: Oct. 1, 1999

(51) Int. Cl.[7] ............... C12N 9/48; C12N 9/50; A61K 38/46
(52) U.S. Cl. ............ 435/212; 435/219; 424/94.67
(58) Field of Search ............... 435/212, 219; 424/94.67

(56) References Cited

U.S. PATENT DOCUMENTS 4,610,879  9/1986  Markland et al. ............... 424/94.67

FOREIGN PATENT DOCUMENTS 0 323 722  7/1989  (EP) .

OTHER PUBLICATIONS

Guan et al., Archives of Biochemistry and Biophysics, vol. 289, No. 2, pp. 197–207 (1991).
Randolph et al., Protein Science, , vol. 1, pp. 590–600 (1992).
Markland et al., Circulation, vol. 90, No. 5, pp. 2448–2456 (1994).
Loayza et al., Journal of Chromatography B 662, pp. 227–243 (19940.
Rholam et al., European Journal of Biochemistry, vol. 227, pp. 707–714 (1995).

Primary Examiner—Ponnathapu Achutamurthy
Assistant Examiner—Peter P. Tung
(74) Attorney, Agent, or Firm—Richard J. Mazza; Ron K. Levy; Steven M. Odre

(57) ABSTRACT

A fibrinolytically active metalloproteinase polypeptide (called "novel acting thrombolytic") which is useful for blood clot lysis in vivo and methods and materials for its production by recombinant expression are described.

2 Claims, 1 Drawing Sheet

FIGURE 1

MRFPSIFTAV LFAASSALAA PVNTTTEDET AQIPAEAVIG
YSDLEGDFDV AVLPFSNSTN NGLLFINTTI ASIAAKEEGV
SLEKREAEAS SIILESGNVN DYEVVYPRKV TPVPRGAVQP
KYEDAMQYEF KVNSEPVVLH LEKNKGLFSE DYSETHYSPD
GREITTYPLG EDHCYYHGRI ENDADSTASI SACNGLKGHF
KLQGEMYLIE PLELSDSEAH AVYKYENVEK EDEAPKMCGV
TQNWESYEPI KKAFQLNLTK RSFPQRYVQL VIVADHRMNT
KYNGDSDKIR QWVHQIVNTI NEIYRPLNIQ FTLVGLEIWS
NQDLITVTSV SHDTLASFGN WRETDLLRRQ RHDNAQLLTA
IDFDGDTVGL AYVGGMCQLK HSTGVIQDHS AINLLVALTM
AHELGHNLGM NHDGNQCHCG ANSCVMAAML SDQPSKLFSD
CSKKDYQTFL TVNNPQCILN KP

FIBRONOLYTICALLY ACTIVE POLYPEPTIDE

FIELD OF THE INVENTION

This invention relates to a fibrinolytically active metalloproteinase of non-naturally occurring sequence, to combinant methods for its manufacture, and to its use in treating thrombosis in vivo.

BACKGROUND OF THE INVENTION

Fibrolase is an enzymatically active polypeptide (specifically, a metalloproteinase) composed of 203 amino acid residues that was originally isolated by purification from the venom of the Southern Copperhead snake; U.S. Pat. No. 4,610,879, issued Sep. 9, 1986 (Markland et al.); and Guan et al., Archives of Biochemistry and Biophysics, Volume 289, Number 2, pages 197–207 (1991). The enzyme exhibits direct fibrinolytic activity with little or no hemorrhagic activity, and it dissolves blood clots made either from fibrinogen or from whole blood.

The amino acid sequence of fibrolase has also been determined, with methods described for recombinant production in yeast and use for the treatment of thrombembolic conditions in vivo; Randolph et al., Protein Science, Cambridge University Press (1992), pages 590–600, and European Patent Application No. 0 323 722 (Valenzuela et al.), published Jul. 12, 1989.

SUMMARY OF THE INVENTION

This invention provides a fibinolytic metalloproteinase having the non-naturally occurring linear array of amino acids depicted in SEQ ID NO: 1, also referred to herein as "novel acting thrombolytic" (or "NAT"). Also provided are nucleic acid molecules, such as the one of SEQ ID NO: 2 and variants thereof encoding NAT.

The term "mature" is used in its conventional sense to refer to the biologically active polypeptide which has been enzymatically processed in situ in the host cell to cleave it from the prepro region.

Because of its fibrinolytic activity, NAT is useful in vivo as a blood clot lysing agent to treat thrombosis in a mammal (including rats, pigs and humans).

The NAT polypeptide of this invention provides advantages over naturally occurring fibrolase as a therapeutic agent (i.e., the fibrinolytic polypeptide found in snake venom). Native fibrolase is known to contain several alternate N-termini: QQRFP (amino acids 1–5 of SEQ ID NO: 5), EQRFP (amino acids 1–5 of SEQ ID NO: 15) and ERFP (amino acids 1–4 of SEQ ID NO: 16) (in which "E" designates a cyclized glutamine, or pyroglutamic acid). More specifically, starting with an N-terminus composed of QQRFP (see SEQ ID NO: 5), the fibrolase molecule undergoes degradation to result in two isoforms, having N-terminal sequences of EQRFP (see SEQ ID NO: 15) and ERFP (see SEQ ID NO: 16), respectively. Recombinant fibrolase as produced in yeast typically yields a mixture of all three of these forms and is thus not homogeneous. See Loayza et al., Journal of Chromatography, B 662, pages 227–243 (1994). Moreover, the cyclized glutamine residue results in a "blocked" N-terminus which makes sequencing impossible.

In contrast, the recombinant NAT of this invention provides a single species: only one N-terminus is typically produced. The result is greater homogeneity of the end product compared to recombinant fibrolase, which is beneficial when medical applications are the intended end use.

BRIEF DESCRIPTION OF THE FIGURES

FIG. 1 depicts in linear fashion the full amino acid sequence of NAT (SEQ ID NO: 3), consisting of the "prepro" region (underscored), which includes the "signal" peptide, and the mature polypeptide (non-underscored).

DETAILED DESCRIPTION OF THE INVENTION

NAT may be produced by recombinant expression of the nucleic acid molecule of SEQ ID NO: 4, which encodes the full amino acid sequence of NAT (SEQ ID NO: 3), including the prepro region from nucleotides 1–783 and mature polypeptide from nucleotides 784–1386, in a suitable host. Following expression, the prepro region is enzymatically processed off in the host cell to yield the mature active polypeptide (SEQ ID NO: 1).

Preferably, NAT is produced recombinantly in yeast, as will be explained in greater detail further below.

The mature polypeptide (SEQ ID NO: 1) which is thus produced may or may not have an amino terminal methionine, depending on the manner in which it is prepared. Typically, an amino terminal methionine residue will be present when the polypeptide is produced recombinantly in a non-secreting bacterial (e.g., E. coli) strain as the host.

Besides the nucleic acid molecule of SEQ ID NO: 2, also utilizable are degenerate sequences thereof which encode the same polypeptide. The present invention also embraces nucleic acid molecules that may encode additional amino acid residues flanking the 5' or 3' portions of the region encoding the mature polypeptide, such as sequences encoding alternative pre/pro regions (i.e., sequences responsible for secretion of the polypeptide through cell membranes) in place of the "native" pre/pro region (i.e., found in naturally occurring fibrolase). The additional sequences may also be noncoding sequences, including regulatory sequences such as promoters of transcription or translation, depending on the host cell.

NAT can be prepared using well known recombinant DNA technology methods, such as those set forth in Sambrook et al., Molecular Cloning: A Laboratory Manual, Cold Spring Harbor Laboratory Press, Cold Spring Harbor, N.Y. (1989) and/or Ausubel et al., editors, Current Protocols in Molecular Biology, Green Publishers Inc. and Wiley and Sons, New York (1994). A DNA molecule encoding the polypeptide or truncated version thereof may be obtained, for example, by screening a genomic or cDNA library, or by PCR amplification, to obtain a nucleic acid molecule encoding fibrolase, followed by replacement of the codons encoding the N-terminal amino acid residues QQR with a codon for serine (S). Alternatively, a DNA molecule encoding NAT may be prepared by chemical synthesis using methods well known to the skilled artisan, such as those described by Engels et al. in Angew. Chem. Intl. Ed., Volume 28, pages 716–734 (1989). Typically, the DNA will be several hundred nucleotides in length. Nucleic acids larger than about one hundred nucleotides can be synthesized as several fragments using these same methods and the fragments can then be ligated together to form a nucleotide sequence of the desired length.

The DNA molecule is inserted into an appropriate expression vector for expression in a suitable host cell. The vector is selected to be functional in the particular host cell employed (i.e., the vector is compatible with the host cell machinery, such that expression of the DNA can occur). The polypeptide may be expressed in prokaryotic, yeast, insect (baculovirus systems) or eukaryotic host cells, although yeast is preferred as will be explained in greater detail further below.

The vectors used in any of the host cells to express NAT may also contain a 5' flanking sequence (also referred to as a "promoter") and other expression regulatory elements operatively linked to the DNA to be expressed, as well as enhancer(s), an origin of replication element, a transcriptional termination element, a complete intron sequence containing a donor and acceptor splice site, a signal peptide sequence, a ribosome binding site element, a polyadenylation sequence, a polylinker region for inserting the nucleic acid encoding NAT, and a selectable marker element. Each of these elements is discussed below.

Optionally, the vector may also contain a "tag" sequence, i.e., an oligonucleotide sequence located at the 5' or 3' end of the polypeptide-coding sequence that encodes polyHis (such as hexaHis) or another small immunogenic sequence (such as the c-myc or hemagglutinin epitope, for which antibodies, including monoclonal antibodies, are commercially available). This tag will be expressed along with NAT, and can serve as an affinity tag for purification of this polypeptide from the host cell. Optionally, the tag can subsequently be removed from the purified polypeptide by various means, for example, with use of a selective peptidase.

The 5' flanking sequence may be the native 5' flanking sequence, or it may be homologous (i.e., from the same species and/or strain as the host cell), heterologous (i.e., from a species other than the host cell species or strain), hybrid (i.e., a combination of 5' flanking sequences from more than one source), or synthetic. The source of the 5' flanking sequence may be any unicellular prokaryotic or eukaryotic organism, any vertebrate or invertebrate organism, or any plant, provided that the 5' flanking sequence is functional in, and can be activated by the host cell machinery.

The origin of replication element is typically a part of prokaryotic expression vectors purchased commercially and aids in the amplification of the vector in a host cell. Amplification of the vector to a certain copy number can, in some cases, be important for optimal expression of NAT. If the vector of choice does not contain an origin of replication site, one may be chemically synthesized based on a known sequence, and then ligated into the vector.

The transcription termination element is typically located 3' to the end of the polypeptide coding sequence and serves to terminate transcription of the mRNA. Usually, the transcription termination element in prokaryotic cells is a G-C rich fragment followed by a poly T sequence. While the element is easily cloned from a library or even purchased commercially as part of a vector, it can also be readily synthesized using known methods for nucleic acid synthesis.

A selectable marker gene element encodes a protein necessary for the survival and growth of a host cell grown in a selective culture medium. Typical selection marker genes encode proteins that: (a) confer resistance to antibiotics or other toxins, for example, ampicillin, tetracycline or kanamycin for prokaryotic host cells, zeocin for yeast host cells, and neomycin for mammalian host cells; (b) complement auxotrophic deficiencies of the cell; or (c) supply critical nutrients not available from complex media. Preferred selectable markers for use in prokaryotic expression are the kanamycin resistance gene, the ampicillin resistance gene, and the tetracycline resistance gene.

The ribosome binding element, commonly called the Shine-Dalgarno sequence (for prokaryotes) or the Kozak sequence (for eukaryotes), is necessary for the initiation of translation of mRNA. The element is typically located 3' to the promoter and 5' to the coding sequence of the polypeptide to be synthesized. The Shine-Dalgarno sequence is varied but is typically a polypurine (i.e., having a high A-G content). Many Shine-Dalgarno sequences have been identified, each of which can be readily synthesized using methods set forth above and used in a prokaryotic vector. The Kozak sequence typically includes sequences immediately before and after the initiating codon. A preferred Kozak sequence is one that is associated with a high efficiency of initiation of translation at the AUG start codon.

In those cases where it is desirable for NAT polypeptide to be secreted from the host cell, a signal sequence may be used to direct the polypeptide out of the host cell where it is synthesized. Typically, the signal sequence is positioned in the coding region of nucleic acid sequence, or directly at the 5' end of the coding region. Many signal sequences have been identified, and any of them that are functional in the selected host cell may be used here. Consequently, the signal sequence may be homologous or heterologous to the polypeptide. Additionally, the signal sequence may be chemically synthesized using methods referred to above.

After the vector has been constructed and a nucleic acid has been inserted into the proper site of the vector, the completed vector may be inserted into a suitable host cell for amplification and/or polypeptide expression.

As mentioned, host cells may be prokaryotic (such as *E. coli*) or eukaryotic (such as a yeast cell, an insect cell, or a vertebrate cell). The host cell, whether it be yeast or some other host, when cultured under appropriate conditions can synthesize NAT, which can subsequently be collected from the culture medium (if the host cell secretes it into the medium) or directly from the host cell producing it (if it is not secreted). After collection, NAT polypeptide can be purified using methods such as molecular sieve chromatography, affinity chromatography, and the like.

Selection of the host cell will depend in large part on whether the manner in which the host cell is able to "fold" NAT into its native secondary and tertiary structure (e.g., proper orientation of disulfide bridges, etc.) such that biologically active material is prepared by the cell. However, even where the host cell does not synthesize biologically active material, it may be "folded" after synthesis using appropriate chemical conditions, such as ones that are known to those skilled in the art. In either case, proper folding can be inferred from the fact that biologically active material has been obtained.

Suitable host cells or cell lines may be mammalian cells, such as Chinese hamster ovary cells (CHO) or 3T3 cells. The selection of suitable mammalian host cells and methods for transformation, culture, amplification, screening and product production and purification are known in the art. Other suitable mammalian cell lines are the monkey COS-1 and COS-7 cell lines, and the CV-1 cell line. Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Still other suitable mammalian cell lines include but are not limited to, HeLa, mouse L-929 cells, 3T3 lines derived from Swiss, Balb-c or NIH mice, BHK or HaK hamster cell lines.

Also useful as host cells are bacterial cells. For example, the various strains of *E. coli* (e.g., HB101, DH5a, DH10, and MC1061) are well-known as host cells in the field of biotechnology. Various strains of *B. subtilis*, Pseudomonas spp., other Bacillus spp., Streptomyces spp., and the like, may also be employed. Additionally, many strains of yeast cells known to those skilled in the art are also available as host cells for expression of the polypeptide of the present invention. Also, where desired, insect cells may be utilized as host cells. See, for example, Miller et al., Genetic Engineering, Volume 8, pages 277–298 (1986).

Insertion (also referred to as "transformation" or "transfection") of the vector into the selected host cell may be accomplished using such methods as calcium phosphate, electroporation, microinjection, lipofection or the DEAE-dextran method. The method selected will in part be a function of the type of host cell to be used. These methods and other suitable methods are well known to the skilled artisan, and are set forth, for example, in Sambrook et al., above.

The host cells containing the vector may be cultured using standard media well known to the skilled artisan. The media will usually contain all nutrients necessary for the growth and survival of the cells. Suitable media for culturing *E. coli* cells are, for example, Luria Broth (LB) and/or Terrific Broth (TB). Suitable media for culturing eukaryotic cells are RPMI 1640, MEM, DMEM, all of which may be supplemented with serum and/or growth factors as required by the particular cell line being cultured. A suitable medium for insect cultures is Grace's medium supplemented with yeastolate, lactalbumin hydrolysate and/or fetal calf serum, as necessary.

Typically, an antibiotic or other compound useful for selective growth of the transformed cells only is added as a supplement to the media. The compound to be used will be dictated by the selectable marker element present on the plasmid with which the host cell was transformed. For example, where the selectable marker element is kanamycin resistance, the compound added to the culture medium will be kanamycin.

The amount of NAT produced in the host cell can be evaluated using standard methods known in the art. Such methods include, without limitation, Western blot analysis, SDS-polyacrylamide gel electrophoresis, non-denaturing gel electrophoresis, HPLC separation, immunoprecipitation, and/or activity assays such as DNA binding gel shift assays.

If NAT is secreted from the host cells other than gram-negative bacteria, the majority will likely be found in the cell culture medium. If NAT is secreted from gram-negative bacteria, it will to some degree be found in the periplasm. If NAT is not secreted, it will be present in the cytoplasm.

For intracellular NAT, the host cells are typically first disrupted mechanically. For NAT having a periplasmic location, either mechanical disruption or osmotic treatment can be used to release the periplasmic contents into a buffered solution. NAT polypeptide is then isolated from this solution. Purification from solution can thereafter be accomplished using a variety of techniques. If NAT has been synthesized so that it contains a tag such as hexahistidine or other small peptide at either its carboxyl or amino terminus, it may essentially be purified in a one-step process by passing the solution through an affinity column where the column matrix has a high affinity for the tag or for the polypeptide directly (i.e., a monoclonal antibody). For example, polyhistidine binds with great affinity and specificity to nickel, thus an affinity column of nickel (such as the Qiagen nickel columns) can be used for purification. (See, for example, Ausubel et al., editors, Current Protocols in Molecular Biology, above).

Where, on the other hand, the polypeptide has no tag and no antibodies are available, other well known procedures for purification can be used. Such procedures include, without limitation, ion exchange chromatography, molecular sieve chromatography, reversed phase chromatography, HPLC, native gel electrophoresis in combination with gel elution, and preparative isoelectric focusing (ISOPRIME® isoelectric protein purification apparatus, Hoefer Pharmacia Biotech Inc.). In some cases, two or more of these techniques may be combined to achieve increased purity.

Especially preferred for use in the production of NAT are yeast cells, and most advantageously those of the yeast genus known as Pichia (e.g., *Pichia pastoris*), because of the greater efficiency of refolding compared to, for instance, bacterial cells such as *E. coli*. Suitable recombinant methods of expression for this yeast strain are described in U.S. Pat. No. 4,855,231 (Stroman et al.), U.S. Pat. No. 4,812,405 (Lair et al.), U.S. Pat. No. 4,818,700 (Cregg et al.), U.S. Pat. No. 4,885,242 (Cregg) and U.S. Pat. No. 4,837,148 (Cregg), the disclosures of which are incorporated herein by reference.

Notably, Pichia cells can also be used to express fibrolase with similar efficiency from DNA molecules encoding this metalloproteinase, and such a method constitutes an additional aspect of the present invention. Fibrolase is a known metalloproteinase which has been described in the scientific and patent literature; see Randolph et al., and European Patent Application No. 0 323 722, cited above. Typically, the fibrolase to be expressed will be of SEQ ID NO: 5, which is encoded by the cDNA molecule of SEQ ID NO: 6 (or variants thereof encoding the same amino acid sequence). The expression of fibrolase in such a system will typically involve a DNA molecule of SEQ ID NO: 7, which encodes "prepro" sequence (nucleotides 1–783) in addition to the "mature" polypeptide (nucleotides 784–1392).

Chemically modified versions of NAT in which the polypeptide is linked to a polymer or other molecule to form a derivative in order to modify properties are also included within the scope of the present invention. For human therapeutic purposes especially, it may be advantageous to derivatize NAT in such a manner by the attachment of one or more other chemical moieties to the polypeptide moiety. Such chemical moieties may be selected from among various water soluble polymers. The polymer should be water soluble so that the NAT polypeptide to which it is attached is miscible in an aqueous environment, such as a physiological environment. The water soluble polymer may be selected from the group consisting of, for example, polyethylene glycol, copolymers of ethylene glycol/propylene glycol, carboxymethylcellulose, dextran, polyvinyl alcohol, polyvinyl pyrolidone, poly-1,3-dioxolane, poly-1,3,6-trioxane, ethylene/maleic anhydride copolymer, polyaminoacids (either homopolymers or random or non-random copolymers (see further below regarding fusion molecules), and dextran or poly(n-vinyl pyrolidone)polyethylene glycol, propylene glycol homopolymers, polypropylene oxide/ethylene oxide co-polymers, polyoxyethylated polyols, polystyrenemaleate and polyvinyl alcohol. Polyethylene glycol propionaldenhyde may have advantages in manufacturing due to its stability in water.

The polymer may be of any molecular weight, and may be branched or unbranched. For polyethylene glycol, the preferred molecular weight is between about 2 kilodaltons (kDa) and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol on a therapeutic protein).

The number of polymer molecules so attached may vary, and one skilled in the art will be able to ascertain the effect on function. One may mono-derivatize, or may provide for a di-, tri-, tetra- or some combination of derivatization, with the same or different chemical moieties (e.g., polymers, such as different weights of polyethylene glycols). The proportion of polymer molecules to NAT polypeptide molecules will vary, as will their concentrations in the reaction mixture. In general, the optimum ratio (in terms of efficiency of reaction in that there is no excess unreacted polypeptide or polymer) will be determined by factors such as the desired degree of derivatization (e.g., mono, di-, tri-, etc.), the molecular weight of the polymer selected, whether the polymer is branched or unbranched, and the reaction conditions.

The chemical moieties should be attached to NAT with consideration of effects on functional or antigenic domains of the polypeptide. There are a number of attachment methods available to those skilled in the art. See, for example, EP 0 401 384 (coupling PEG to G-CSF), and Malik et al., Experimental Hematology, Volume 20, pages 1028–1035 (1992) (reporting the pegylation of GM-CSF using tresyl chloride). By way of illustration, polyethylene glycol may be covalently bound through amino acid residues via a reactive group, such as, a free amino or carboxyl group. Reactive groups are those to which an activated polyethylene glycol molecule (or other chemical moiety) may be bound. The amino acid residues having a free amino group may include lysine residues and the N-terminal amino acid residue. Those having a free carboxyl group may include aspartic acid residues, glutamic acid residues, and the C-terminal amino acid residue. Sulfhydryl groups may also be used as a reactive group for attaching the polyethylene glycol molecule(s) (or other chemical moiety). Preferred for manufacturing purposes is attachment at an amino group, such as at the N-terminus or to a lysine group. Attachment at residues important for receptor binding should be avoided if receptor binding is desired.

One may specifically desire N-terminally chemically modified derivatives. Using polyethylene glycol as an illustration, one may select from a variety of polyethylene glycol molecules (by molecular weight, branching, etc.), the proportion of polyethylene glycol molecules to polypeptide molecules in the reaction mixture, the type of pegylation reaction to be performed, and the method of obtaining the selected N-terminally pegylated NAT. The method of obtaining the N-terminally pegylated preparation (i.e., separating this moiety from other monopegylated moieties if necessary) may be by purification of the N-terminally pegylated material from a population of pegylated NAT molecules. Selective N-terminal chemical modification may be accomplished by reductive alkylation which exploits differential reactivity of different types of primary amino groups (lysine versus the N-terminal) available for derivatization. See PCT application WO 96/11953, published Apr. 25, 1996. Under the appropriate reaction conditions, substantially selective derivatization of NAT at the N-terminus with a carbonyl group containing polymer is achieved. For example, one may selectively N-terminally pegylate NAT by performing the reaction at a pH which allows one to take advantage of the $pK_a$ differences between the $\epsilon$-amino group of the lysine residues and that of the $\alpha$-amino group of the N-terminal residue of the polypeptide. By such selective derivatization, attachment of a polymer to a polypeptide is controlled: the conjugation with the polymer takes place predominantly at the N-terminus of the polypeptide and no significant modification of other reactive groups, such as lysine side chain amino groups, occurs. Using reductive alkylation, the polymer may be of the type described above, and should have a single reactive aldehyde for coupling to the polypeptide. Polyethylene glycol propionaldehyde, containing a single reactive aldehyde, may be used.

NAT or chemically modified derivatives in accordance with the invention may be formulated for in vivo administration, and most preferably via intrathrombus (i.e., via localized delivery directly to the site of the clot in the blood vessel, e.g., as by catheter). Systemic delivery is normally not preferred due to the likelihood that innate $\alpha 2$ macroglobulin in the general circulation may complex with NAT to prevent interaction with fibrin or fibrinogen, thus impairing clot lysis. However, there may be instances where larger amounts of NAT can be used which exceed the circulating levels of $\alpha 2$ macroglobulin, thus enabling systemic administration and delivery. In general, encompassed within the invention are pharmaceutical compositions comprising effective amounts of NAT together with pharmaceutically acceptable diluents, preservatives, solubilizers, emulsifiers, adjuvants and/or carriers. By "effective amount" is meant amount sufficient to produce a measurable biological effect (i.e., a thrombolytically effective amount which effects lysis of the blood clot or clots being treated).

Typically, NAT will be in highly purified form, and any pharmaceutical composition being used as the delivery vehicle will normally be presterilized for use, such as by filtration through sterile filtration membranes.

One skilled in the art will be able to ascertain effective dosages by administration and observing the desired therapeutic effect. Particular effective doses within this range will depend on the particular disorder or condition being treated, as well as the age and general health of the recipient, and can be determined by standard clinical procedures. Where possible, it will be desirable to determine the dose-response curve of the pharmaceutical composition first in vitro, as in bioassay systems, and then in useful animal model systems in vivo prior to testing in humans. The skilled practitioner, considering the therapeutic context, type of disorder under treatment, and other applicable factors, will be able to ascertain proper dosing without undue effort. Typically, a practitioner will administer the NAT composition until a dosage is reached that achieves the desired effect (i.e., lysis of the blood clot). The composition may be administered as a single dose, or as two or more doses (which may or may not contain the same amount of polypeptide) over time, or on a continuous basis.

NAT may also be used to generate antibodies in accordance with standard methods. The antibodies may be polyclonal, monoclonal, recombinant, chimeric, single-chain and/or bispecific, etc. To improve the likelihood of producing an immune response, the amino acid sequence of NAT can be analyzed to identify portions of the molecule that may be associated with increased immunogenicity. For example, the amino acid sequence may be subjected to computer analysis to identify surface epitopes, such as in accordance with the method of Hope and Woods, Proceedings of the National Academy of Science USA, Volume 78, pages 3824–3828 (1981).

Various procedures known in the art can be used for the production of polyclonal antibodies which recognize epitopes of NAT. For the production of antibody, various host animals can be immunized by injection with the polypeptide, including but not limited to rabbits, mice, rats, etc. Various adjuvants may be used to increase the immunological response, depending on the host species, including but not limited to Freund's, mineral gels such as aluminum hydroxide (alum), surface active substances such as lysolecithin, pluronic polyols, polyanions, peptides, oil emulsions, keyhole limpet hemocyanins, dinitrophenol, and potentially useful human adjuvants such as Bacille Calmette-Guerin and *Corynebacterium parvum*.

For the preparation of monoclonal antibodies directed toward NAT, any technique which provides for the production of antibody molecules by continuous cell lines in culture may be used. For example, the hybridoma technique originally developed by Kohler and Milstein which is described in Nature, Volume 256, pages 495–497 (1975), as well as the trioma technique, the human B-cell hybridoma technique described by Kozbor et al. in Immunology Today, Volume 4, page 72 (1983), and the EBV-hybridoma technique to produce monoclonal antibodies described by Cole et al. in "Monoclonal Antibodies and Cancer Therapy", Alan R. Liss, Inc., pages 77–96 (1985), are all useful for preparation of monoclonal antibodies in accordance with this invention.

The antibodies of this invention can be used therapeutically, such as to bind to and thereby neutralize or inhibit excess amounts of NAT in vivo after administration. The antibodies can further be used for diagnostic purposes, such as in labeled form to detect the presence of NAT in a body fluid, tissue sample or other extract, in accordance with known diagnostic methods.

DESCRIPTION OF SPECIFIC EMBODIMENTS

The invention is further illustrated in the following examples.

EXAMPLE 1
Derivation of NAT Sequence

An effective way to produce fibrolase is to express it initially as preprofibolase in which cleavage by the protease kex-2 occurs at the junction of the "prepro" and "mature" regions to yield biologically active material ("mature" fibrolase). From this design, the synthesis and processing of the preprofibrolase leads to secretion of mature fibrolase into the culture medium. The actual sequence at the cleaved junction is ( . . . TKR↓QQRF . . . ) comprising amino acids 259–265 of SEQ ID NO: 14.

Kex-2 is an endoprotease that cleaves after two adjacent basic amino acids, in this case lysine(K)-arginine(R). Mature fibrolase expressed from DNA having the above mentioned sequence revealed that the expected N-terminal glutamine (Q) residue had in fact undergone deamidation and cyclization to generate pyroglutamic acid (E). This chemical modification was deemed undesirable, since peptides with an N-terminal cyclized glutamine (pyroglutamic acid) residue fail to react in the Edman degradation procedure for amino acid sequencing. Accordingly, both of the glutamine (Q) residues at the N-terminus in the sequence for mature fibrolase (amino acids 1–2 of SEQ ID NO: 5) were deleted, resulting in an N-terminal arginine (R) residue. Since kex-2 cleaves after two adjacent basic amino acids as mentioned, it was anticipated that the sequence ( . . . KRRF . . . ) (SEQ ID NO: 21) would present an ambiguous site for kex-2 cleavage. Accordingly, the N-terminal arginine (R) residue (shown underlined above) was replaced with a serine (S) residue to result in the sequence ( . . . KRSF . . . ) see amino acids 260–263 of SEQ ID NO 17. The choice of serine was based on the need to introduce an amino acid which facilitates kex-2 cleavage when it occurs on the C-terminal side of the hydolysis site. Rholam et al., European Journal of Biochemistry, Volume 227, pages 707–714 (1995).

As a result, the DNA sequence for preprofibrolase was modified by site-directed mutagenesis at the N-terminal coding region for mature fibrolase to substitute the codons for "QQR" with a codon for "S", using a standard PCR protocol, thus resulting in preproNAT having the amino acid sequence of SEQ ID NO: 3. The oligonucleotides used to prime the PCR reactions are listed below, and their homology with the target sequence is also shown. Initially, two PCR reactions were carried out using oligos 1 and 4 as one primer pair and oligos 2 and 3 as another primer pair, both with DNA of the parent gene as the template. The DNA products of these two reactions (602 and 816 nucleotides in length) were purified by agarose gel which are SEQ ID NOs: 18 and 19, respectively, electrophoresis and combined to serve as a template in a second round of PCR using oligos 1 and 2 as the primer pair. This final PCR product (1373 nucleotides in length) was cleaved with restriction endonucleases which is SEQ ID NO: 20 XhoI and NotI. The digest was deproteinized with phenol/chloroform and DNA precipitated. A portion of the recovered DNA was ligated into the plasmid pPICZα (Invitrogen, Carlsbad, Calif., Catalog No. VI95-20), which had been similarly cleaved with restriction endonucleases XhoI and NotI, enzymatically dephosphorylated, and deproteinized with phenol/chloroform. All subsequent steps were carried out according to the Invitrogen Pichia Expression Kit manual (Invitrogen Corp., Catalog No. K1710-01). The ligation reaction products were transformed into *E. coli* by electroporation and selected for survival on zeocin-containing solid media. The plasmid was isolated and the profibrolase region was confirmed by DNA sequencing. The plasmid was linearized by cleaving with restriction endonuclease PmeI and then transformed into *Pichia pastoris* GS115his+. The GS115 strain is normally his−, so the his genotype was restored by transformation with a DNA source carrying the wild type version of the his4 gene. Alternatively, a his+ strain can be obtained commercially from Invitrogen Corp.(X-33 cell line, Catalog No. C180-00). Integrants were selected as zeocin-resistant colonies. Candidate clones were induced in methanol-containing media, and the broth was assayed for NAT production on 4–20% PAGE, using Coomassie staining.

The oligonucleotides used for site-directed PCR mutagenesis were as follows:

Oligo 1 5'-TACTATTGCCAGCATTGCTGC-3'    (SEQ ID NO: 8)

Oligo 2 5'-GCAAATGGCATTCTGACATCC-3'    (SEQ ID NO: 9)

Oligo 3 5'-TCCAATTAAACTTGACTAA-
GAGATCTTTCCCACAAAGATACGTAC-3' (SEQ ID NO: 10)

Oligo 4 5'-GTACGTATCTTTGTGGGAAAGATCTCT-
TAGTCAAGTTTAATTGG-3'    (SEQ ID NO: 11)

The location of these oligonucleotides is shown below in relation to the double-stranded DNA sequence (SEQ ID NO: 12 coding or sense strand, SEQ ID NO: 13 complementary or antisense strand) and corresponding amino acid sequences (SEQ ID NO: 14, SEQ ID NO: 22, SEQ ID NO: 23, SEQ ID NO: 24, SEQ ID NO: 25) of fibrolase (including the prepro region) being modified to create NAT. The N-terminal and C-terminal regions of mature fibrolase are indicated by underlining of terminal amino acid sequences (QQRF and LNKP)(nucleotides 262–265 and 461–464 of SEQ ID NO: 14). The N-terminal region (QQRF) is the one being modified (to substitute S for QQR). For oligos 3 and 4, below, dashed lines are inserted to denote the location of the omitted codons encoding for residues QQ in the N-terminal region of fibrolase.

```
ATGAGATTTCCTTCAATTTTTACTGCTGTTTTATTCGCAGCATCCTCCGCATTAGCTGCT
---------+---------+---------+---------+---------+---------+
TACTCTAAAGGAAGTTAAAAATGACGACAAAATAAGCGTCGTAGGAGGCGTAATCGACGA

M   R   F   P   S   I   F   T   A   V   L   F   A   A   S   S   A   L   A   A

CCAGTCAACACTACAACAGAAGATGAAACGGCACAAATTCCGGCTGAAGCTGTCATCGGT
---------+---------+---------+---------+---------+---------+
GGTCAGTTGTGATGTTGTCTTCTACTTTGCCGTGTTTAAGGCCGACTTCGACAGTAGCCA

P   V   N   T   T   E   D   E   T   A   Q   I   P   A   E   A   V   I   G

TACTCAGATTTAGAAGGGGATTTCGATGTTGCTGTTTTGCCATTTTCCAACAGCACAAAT
---------+---------+---------+---------+---------+---------+
ATGAGTCTAAATCTTCCCCTAAAGCTACAACGACAAAACGGTAAAAGGTTGTCGTGTTTA

Y   S   D   L   E   G   D   F   D   V   A   V   L   P   F   S   N   S   T   N

Oligo 1     5'-TACTATTGCCAGCATTGCTGC-3'
AACGGGTTATTGTTTATAAATACTACTATTGCCAGCATTGCTGCTAAAGAAGAAGGGGTA
---------+---------+---------+---------+---------+---------+
TTGCCCAATAACAAATATTTATGATGATAACGGTCGTAACGACGATTTCTTCTTCCCCAT

N   G   L   L   F   I   N   T   T   I   A   S   I   A   A   K   E   E   G   V

XhoI
 |
TCTCTCGAGAAAAGAGAGGCTGAAGCTTCTTCTATTATCTTGGAATCTGGTAACGTTAAC
---------+---------+---------+---------+---------+---------+
AGAGAGCTCTTTTCTCTCCGACTTCGAAGAAGATAATAGAACCTTAGACCATTGCAATTG

S   L   E   K   R   E   A   E   A   S   S   I   I   L   E   S   G   N   V   N

GATTACGAAGTTGTTTATCCAAGAAAGGTCACTCCAGTTCCTAGGGGTGCTGTTCAACCA
---------+---------+---------+---------+---------+---------+
CTAATGCTTCAACAAATAGGTTCTTTCCAGTGAGGTCAAGGATCCCCACGACAAGTTGGT

D   Y   E   V   V   Y   P   R   K   V   T   P   V   P   R   G   A   V   Q   P

AAGTACGAAGATGCCATGCAATACGAATTCAAGGTTAACAGTGAACCAGTTGTCTTGCAC
---------+---------+---------+---------+---------+---------+
TTCATGCTTCTACGGTACGTTATGCTTAAGTTCCAATTGTCACTTGGTCAACAGAACGTG

K   Y   E   D   A   M   Q   Y   E   F   K   V   N   S   E   P   V   V   L   H

TTGGAAAAAAACAAAGGTTTGTTCTCTGAAGATTACTCTGAAACTCATTACTCCCCAGAT
---------+---------+---------+---------+---------+---------+
AACCTTTTTTGTTTCCAAACAAGAGACTTCTAATGAGACTTTGAGTAATGAGGGGTCTA

L   E   K   N   K   G   L   F   S   E   D   Y   S   E   T   H   Y   S   P   D

GGTAGAGAAATTACTACTTACCCATTGGGTGAAGATCACTGTTACTACCATGGTAGAATC
---------+---------+---------+---------+---------+---------+
CCATCTCTTTAATGATGAATGGGTAACCCACTTCTAGTGACAATGATGGTACCATCTTAG

G   R   E   I   T   T   Y   P   L   G   E   D   H   C   Y   Y   H   G   R   I

GAAAACGATGCTGACTCCACTGCTTCTATCTCTGCTTGTAACGGTTTGAAGGGTCATTTC
---------+---------+---------+---------+---------+---------+
CTTTTGCTACGACTGAGGTGACGAAGATAGAGACGAACATTGCCAAACTTCCCAGTAAAG

E   N   D   A   D   S   T   A   S   I   S   A   C   N   G   L   K   G   H   F

AAGTTGCAAGGTGAAATGTACTTGATTGAACCATTGGAATTGTCCGACTCTGAAGCCCAT
---------+---------+---------+---------+---------+---------+
TTCAACGTTCCACTTTACATGAACTAACTTGGTAACCTTAACAGGCTGAGACTTCGGGTA

K   L   Q   G   E   M   Y   L   I   E   P   L   E   L   S   D   S   E   A   H

GCTGTCTACAAGTACGAAAACGTCGAAAAGGAAGATGAAGCCCCAAAGATGTGTGGTGTT
---------+---------+---------+---------+---------+---------+
CGACAGATGTTCATGCTTTTGCAGCTTTTCCTTCTACTTCGGGGTTTCTACACACCACAA

A   V   Y   K   Y   E   N   V   E   K   E   D   E   A   P   K   M   C   G   V
```

```
                                    -continued
                         Oligo 3   5'-TCCAATTAAACTTGACTAAG
ACCCAAAACTGGGAATCATATGAACCAATCAAGAAGGCCTTCCAATTAAACTTGACTAAG
---------+---------+---------+---------+---------+---------+
TGGGTTTTGACCCTTAGTATACTTGGTTAGTTCTTCCGGAAGGTTAATTTGAACTGATTC
                         Oligo 4   3'-GGTTAATTTGAACTGATTC

T   Q   N   W   E   S   Y   E   P   I   K   K   A   F   Q   L   N   L   T   K

AGA------TCTTTCCCACAAAGATACGTAC-3'
AGACAACAAAGATTCCCACAAAGATACGTACAGCTGCTTATCGTTGCTGACCACCGTATG
---------+---------+---------+---------+---------+---------+
TCTGTTGTTTCTAAGGGTGTTTCTATGCATGTCGACCAATAGCAACGACTGGTGGCATAC
TCT------AGAAAGGGTGTTTCTATGCATG-5'

R   Q   Q   R   F   P   Q   R   Y   V   Q   L   V   I   V   A   D   H   R   M

AACACTAAATACAACGGTGACTCTGACAAAATCCGTCAATGGGTGCACCAAATCGTCAAC
---------+---------+---------+---------+---------+---------+
TTGTGATTTATGTTGCCACTGAGACTGTTTTAGGCAGTTACCCACGTGGTTTAGCAGTTG

N   T   K   Y   N   G   D   S   D   K   I   R   Q   W   V   H   Q   I   V   N

ACCATTAACGAAATCTACAGACCACTGAACATCCAATTCACTTTGGTTGGTTTGGAAATC
---------+---------+---------+---------+---------+---------+
TGGTAATTGCTTTAGATGTCTGGTGACTTGTAGGTTAAGTGAAACCAACCAAACCTTTAG

T   I   N   E   I   Y   R   P   L   N   I   Q   F   T   L   V   G   L   E   I

TGGTCCAACCAAGATTTGATCACCGTTACTTCTGTATCCCACGACACTCTGGCATCCTTC
---------+---------+---------+---------+---------+---------+
ACCAGGTTGGTTCTAAACTAGTGGCAATGAAGACATAGGGTGCTGTGAGACCGTAGGAAG

W   S   N   Q   D   L   I   T   V   T   S   V   S   H   D   T   L   A   S   F

GGTAACTGGCGTGAAACCGACCTGCTGCGTCGCCAACGTCATGATAACGCTCAACTGCTG
---------+---------+---------+---------+---------+---------+
CCATTGACCGCACTTTGGCTGGACGACGCAGCGGTTGCAGTACTATTGCGAGTTGACGAC

G   N   W   R   E   T   D   L   L   R   R   Q   R   H   D   N   A   Q   L   L

ACCGCTATCGACTTCGACGGTGATACTGTTGGTCTGGCTTACGTTGGTGGCATGTGTCAA
---------+---------+---------+---------+---------+---------+
TGGCGATAGCTGAAGCTGCCACTATGACAACCAGACCGAATGCAACCACCGTACACAGTT

T   A   I   D   F   D   G   D   T   V   G   L   A   Y   V   G   G   M   C   Q

CTGAAACATTCTACTGGTGTTATCCAGGACCACTCCGCTATTAACCTGCTGGTTGCTCTG
---------+---------+---------+---------+---------+---------+
GACTTTGTAAGATGACCACAATAGGTCCTGGTGAGGCGATAATTGGACGACCAACGAGAC

L   K   H   S   T   G   V   I   Q   D   H   S   A   I   N   L   L   V   A   L

ACCATGGCACACGAACTGGGTCATAACCTGGGTATGAACCACGATGGCAACCAGTGTCAC
---------+---------+---------+---------+---------+---------+
TGGTACCGTGTGCTTGACCCAGTATTGGACCCATACTTGGTGCTACCGTTGGTCACAGTG

T   M   A   H   E   L   G   H   N   L   G   M   N   H   D   G   N   Q   C   H

TGCGGTGCAAACTCCTGTGTTATGGCTGCTATGCTGTCCGATCAACCATCCAAACTGTTC
---------+---------+---------+---------+---------+---------+
ACGCCACGTTTGAGGACACAATACCGACGATACGACAGGCTAGTTGGTAGGTTTGACAAG

C   G   A   N   S   C   V   M   A   A   M   L   S   D   Q   P   F   K   L   F

TCCGACTGCTCTAAGAAAGACTACCAGACCTTCCTGACCGTTAACAACCCGCAGTGTATC
---------+---------+---------+---------+---------+---------+
AGGCTGACGAGATTCTTTCTGATGGTCTGGAAGGACTGGCAATTGTTGGGCGTCACATAG

S   D   C   S   K   K   D   Y   Q   T   F   L   T   V   N   N   F   Q   C   I

NotI
                |
CTGAACAAACCGTAAGCGGCCGCCAGCTTTCTAGAACAAAAACTCATCTCAGAAGAGGAT
---------+---------+---------+---------+---------+---------+
GACTTGTTTGGCATTCGCCGGCGGTCGAAAGATCTTGTTTTTGAGTAGAGTCTTCTCCTA

L   N   K   P   *   A   A   A   S   F   L   E   Q   K   L   I   S   E   E   D

CTGAATAGCGCCGTCGACCATCATCATCATCATCATTGAGTTTGTAGCCTTAGACATGAC
---------+---------+---------+---------+---------+---------+
```

```
                              -continued
GACTTATCGCGGCAGCTGGTAGTAGTAGTAGTAGTAACTCAAACATCGGAATCTGTACTG

L  N  S  A  V  D  H  H  H  H  H  H  *  V  C  S  L  R  H  D

TGTTCCTCAGTTCAAGTTGGGCACTTACGAGAAGACCGGTCTTGCTAGATTCTAATCAAG
---------+---------+---------+---------+----------+--------+
ACAAGGAGTCAAGTTCAACCCGTGAATGCTCTTCTGGCCAGAACGATCTAAGATTAGTTC

C  S  S  V  Q  V  G  H  L  R  E  D  R  S  C  *  I  L  I  K

AGGATGTCAGAATGCCATTTGCCTGAGAGATGCAGGCTTCATTTTTGATACTTTTTTATT
---------+---------+---------+---------+----------+--------+
TCCTACAGTCTTACGGTAAACGGACTCTCTACGTCCGAAGTAAAAACTATGAAAAAATAA
  CCTACAGTCTTACGGTAAACG-5' Oligo 2

R  M  S  E  C  H  L  P  E  R  C  R  L  H  F  *  Y  F  F  I  -
```

EXAMPLE 2
Expression of NAT in *Pichia pastoris*

When attempts were made to express the DNA for NAT in *E. coli*, very poor refolding and a requirement for dilute conditions reduced the purification efficiency. These and other considerations led to the usage of *Pichia pastoris*, a yeast species, as the host cell. A culture of selected clones of *Pichia pastoris* which had been transfected with prepro NAT cDNA (SEQ ID NO: 4) was inoculated into 500 ml of the following inoculation growth medium:

| Per liter of batch medium | |
|---|---|
| Yeast extract | 30.0 g |
| Potassium phosphate dibasic | 17.2 g |
| Glucose | 20.0 g |
| Biotin | 0.004 g |
| Water | to 1 liter |
| Phosphoric acid, 85% | to adjust pH to 6.00 |

The transfected *P. pastoris* cells were incubated at 30° C. in a shaker for about 30 to 32 hours. About 1% (w/v) of the resulting culture was used to inoculate a 10-liter fermentor. The fermentor contained sterilized basal salts and glucose (below). Twelve milliliters per liter of PTM4 salts (PTM4 is a trace metals solution containing cupric sulfate pentahydrate, sodium iodide, manganese sulfate monohydrate, sodium molybdate dihydrate, boric acid, cobaltous chloride hexahydrate, zinc chloride, ferrous sulfate heptahydrate, d-biotin, sulfuric acid and purified water) were added per liter of batch medium after fermentor sterilization. The fermentation growth temperature was 30° C. The fermentor pH was controlled with ammonium hydroxide and phosphoric acid at pH 6.00. Zinc from the zinc salts added to the medium becomes incorporated into NAT as part of the metalloproteinase structure.

| Basal salts per liter of batch medium | |
|---|---|
| Phosphoric acid, 85% | 26.7 ml |
| Calcium sulfate | 0.93 g |
| Potassium sulfate | 18.2 g |
| Magnesium sulfate-7H$_2$O | 14.9 g |
| Potassium hydroxide | 4.13 g |
| Glucose | 30.0 g |
| Water | to 1 liter |

The batch culture was grown until the glucose was completely consumed (17 to 20 hours). Then a fed-batch phase was initiated. The fed-batch phase media consisted of glucose and 12 ml of PTM4 salts per liter. The induction feed consisted of glucose, 25% methanol, and 12 ml of PTM4 salts per liter. At induction, the temperature of the reactor was shifted to 20° C. The induction phase lasted 60 to 75 hours. The conditioned media were harvested and the cellular debris was discarded.

EXAMPLE 3
Purification of NAT from *Pichia pastoris*

The yeast broth (conditioned media less cellular debris) from Example 2 was clarified and the pH and conductivity were adjusted to 6.5 and 10–20 mS/cm, respectively. The broth was loaded onto an immobilized metal affinity resin that had been charged with copper (Cu) and equilibrated with phosphate buffered saline (PBS). The resin was washed with PBS and eluted with an imidazole gradient (0–100 mM) in PBS. Fractions containing "mature" NAT (SEQ ID NO: 1) were pooled and diluted until the conductivity was less than 1.5 mS/cm, pH 6.4. The diluted pool was loaded onto an SP SEPHAROSE® high molecular weight resin for separation by gel filtration (Amersham Pharmacia Biotech, Inc., Piscataway, N.J.) that had been equilibrated with 10 mM 2-(N-morpholino)ethanesulfonic acid (MES). The column was washed with MES and eluted with a NaCl gradient (0–500 mM) in MES. Fractions containing NAT were pooled and stored.

EXAMPLE 4
Thrombolysis in Acute Thrombosis of Rat Carotid Artery; Comparison of NAT with Urokinase To demonstrate that "mature" NAT (SEQ ID NO: 1) is biologically active and functionally unique, acute pharmacology studies were conducted in rats where focal injury to one of the carotid arteries was created by applying anodal current. This injury produces an occlusive thrombus which generally forms within fifteen minutes. Once the thrombus was formed, the artery was observed for a period of thirty minutes to assure that the carotid occlusion was stable. Then heparin and aspirin were administered intravenously to prevent further propagation of the thrombus. The animals were then treated with an intraarterial infusion of test material. Blood flow through the carotid artery was monitored during the delivery of test material so that successful clot lysis could be detected and the time at which clot lysis occurred could be noted. The percentage of experiments where clot lysis occurred was noted and group means were calculated for only those experiments where clot lysis was successful. As a measure of the hemorrhagic potential of the test material, any blood that was shed from the surgical site was collected with gauze swabs. The swabs were placed in a detergent solution to solubilize red blood cells and release hemoglobin, which was then quantified spectrophotometrically. Shed hemoglobin was used to calculate a volume of blood loss. Test data are reported in the Table below.

TABLE 1

Incidence of Clot Lysis, Time to Clot Lysis and Surgical Blood Loss (Mean ± std. dev.)

| | INCIDENCE OF LYSIS (%) | TIME TO LYSIS (min) | BLOOD LOSS (ml) |
|---|---|---|---|
| SALINE (n = 6) | 0% (0 of 6) | N/A | 0.10± 0.23 |
| Urokinase 25 U/min (n = 15) | 33% (5 of 15) | 55.3± 15.9 | 1.06± 1.59 |
| Urokinase 250 U/min (n = 15) | 86% (13 of 15) | 33.5± 15.3 | 1.43± 1.45 |
| NAT 2 mg (n = 14) | 78% (11 of 14) | 6.3± 5.8 | 0.96± 0.77 |

These studies establish that NAT is biologically active in an animal model of in vivo clot lysis. Further, clot lysis was achieved in a markedly reduced amount of time and with less blood loss from the surgical site, in comparison with urokinase. Thus, the activity profile of NAT can be distinguished from the plasminogen activator class of thrombolytic agents (represented by urokinase) in that clot lysis with NAT occurs more rapidly and with reduced hemorrhagic complications.

The fibrinolytic activity of NAT is comparable to that of fibrolase. In addition, as mentioned above the stability of the N-terminus of NAT results in a more homogeneous end product upon recombinant expression, which is a distinct advantage (i.e., the N-terminus will not change over time resulting in a mixture of different forms, thus making the polypeptide more stable).

---

What is claimed is:

1. A fibrinolytically active polypeptide having the amino acid sequence of SEQ ID NO: 1.

2. The polypeptide of claim 1 which has been made by recombinant expression in yeast.

* * * * *

UNITED STATES PATENT AND TRADEMARK OFFICE
CERTIFICATE OF CORRECTION

PATENT NO. : 6,261,820 B1
DATED : July 17, 2001
INVENTOR(S) : Boone et al.

It is certified that error appears in the above-identified patent and that said Letters Patent is hereby corrected as shown below:

Title page,
Line 1, change "Fibronolytically" to -- Fibrinolytically --

Column 1,
Line 1, change "Fibronolytically" to -- Fibrinolytically --
Line 30, change "fibinolytic" to -- fibrinolytic --

Column 9,
Line 40, change "preprofibolase" to -- preprofibrolase --

Column 10,
Line 39, change "so the his" to -- so the his$^+$ --

Column 13,
Line 63, change "C G A N S C V M A A M L S D Q P F K L F" to -- C G A N S C V M A A M L S D Q P S K L F --.
Line 69, change "S D C S K K D Y Q T F L T V N N F Q C I" to -- S D C S K K D Y Q T F L T V N N P Q C I --

Signed and Sealed this

Twelfth Day of March, 2002

Attest:

JAMES E. ROGAN
Attesting Officer
Director of the United States Patent and Trademark Office

SEQUENCE LISTING

```
<160> NUMBER OF SEQ ID NOS: 29

<210> SEQ ID NO 1
<211> LENGTH: 201
<212> TYPE: PRT
<213> ORGANISM: Artificial
<220> FEATURE:
<223> OTHER INFORMATION: NAT (analog of fibrolase of Agkistrodon
      Contourtrix)

<400> SEQUENCE: 1

Ser Phe Pro Gln Arg Tyr Val Gln Leu Val Ile Val Ala Asp His Arg
1               5                   10                  15

Met Asn Thr Lys Tyr Asn Gly Asp Ser Asp Lys Ile Arg Gln Trp Val
            20                  25                  30

His Gln Ile Val Asn Thr Ile Asn Glu Ile Tyr Arg Pro Leu Asn Ile
        35                  40                  45

Gln Phe Thr Leu Val Gly Leu Glu Ile Trp Ser Asn Gln Asp Leu Ile
    50                  55                  60

Thr Val Thr Ser Val Ser His Asp Thr Leu Ala Ser Phe Gly Asn Trp
65                  70                  75                  80

Arg Glu Thr Asp Leu Leu Arg Arg Gln Arg His Asp Asn Ala Gln Leu
                85                  90                  95

Leu Thr Ala Ile Asp Phe Asp Gly Asp Thr Val Gly Leu Ala Tyr Val
            100                 105                 110

Gly Gly Met Cys Gln Leu Lys His Ser Thr Gly Val Ile Gln Asp His
        115                 120                 125

Ser Ala Ile Asn Leu Leu Val Ala Leu Thr Met Ala His Glu Leu Gly
    130                 135                 140

His Asn Leu Gly Met Asn His Asp Gly Asn Gln Cys His Cys Gly Ala
145                 150                 155                 160

Asn Ser Cys Val Met Ala Ala Met Leu Ser Asp Gln Pro Ser Lys Leu
```

```
                165                 170                 175
Phe Ser Asp Cys Ser Lys Lys Asp Tyr Gln Thr Phe Leu Thr Val Asn
                180                 185                 190

Asn Pro Gln Cys Ile Leu Asn Lys Pro
        195                 200

<210> SEQ ID NO 2
<211> LENGTH: 603
<212> TYPE: DNA
<213> ORGANISM: Artificial
<220> FEATURE:
<223> OTHER INFORMATION: Native pro-NAT (analog of fibrolase)

<400> SEQUENCE: 2
tctttcccac aaagatacgt acagctggtt atcgttgctg accaccgtat gaacactaaa      60
tacaacggtg actctgacaa aatccgtcaa tgggtgcacc aaatcgtcaa caccattaac     120
gaaatctaca gaccactgaa catccaattc actttggttg gtttggaaat ctggtccaac     180
caagatttga tcaccgttac ttctgtatcc cacgacactc tggcatcctt cggtaactgg     240
cgtgaaaccg acctgctgcg tcgccaacgt catgataacg ctcaactgct gaccgctatc     300
gacttcgacg gtgatactgt tggtctggct tacgttggtg gcatgtgtca actgaaacat     360
tctactggtg ttatccagga ccactccgct attaacctgc tggttgctct gaccatggca     420
cacgaactgg gtcataacct gggtatgaac cacgatggca accagtgtca ctgcggtgca     480
aactcctgtg ttatggctgc tatgctgtcc gatcaaccat ccaaactgtt ctccgactgc     540
tctaagaaag actaccagac cttcctgacc gttaacaacc gcagtgtat cctgaacaaa     600 ccg                                                                  603

<210> SEQ ID NO 3
<211> LENGTH: 462
<212> TYPE: PRT
<213> ORGANISM: Artificial
<220> FEATURE:
<223> OTHER INFORMATION: Native pro-NAT (analog of fibrolase)

<400> SEQUENCE: 3

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Ser Asp Leu Glu Gly Asp Phe
            35                  40                  45

Asp Val Ala Val Leu Pro Phe Ser Asn Ser Thr Asn Asn Gly Leu Leu
        50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Ser Ser Ile Ile Leu Glu Ser
                85                  90                  95

Gly Asn Val Asn Asp Tyr Glu Val Val Tyr Pro Arg Lys Val Thr Pro
                100                 105                 110

Val Pro Arg Gly Ala Val Gln Pro Lys Tyr Glu Asp Ala Met Gln Tyr
            115                 120                 125

Glu Phe Lys Val Asn Ser Glu Pro Val Val Leu His Leu Glu Lys Asn
        130                 135                 140

Lys Gly Leu Phe Ser Glu Asp Tyr Ser Glu Thr His Tyr Ser Pro Asp
145                 150                 155                 160
```

```
Gly Arg Glu Ile Thr Thr Tyr Pro Leu Gly Glu Asp His Cys Tyr Tyr
                165                 170                 175

His Gly Arg Ile Glu Asn Asp Ala Asp Ser Thr Ala Ser Ile Ser Ala
            180                 185                 190

Cys Asn Gly Leu Lys Gly His Phe Lys Leu Gln Gly Glu Met Tyr Leu
            195                 200                 205

Ile Glu Pro Leu Glu Leu Ser Asp Ser Glu Ala His Ala Val Tyr Lys
            210                 215                 220

Tyr Glu Asn Val Glu Lys Glu Asp Glu Ala Pro Lys Met Cys Gly Val
225                 230                 235                 240

Thr Gln Asn Trp Glu Ser Tyr Glu Pro Ile Lys Lys Ala Phe Gln Leu
                245                 250                 255

Asn Leu Thr Lys Arg Ser Phe Pro Gln Arg Tyr Val Gln Leu Val Ile
            260                 265                 270

Val Ala Asp His Arg Met Asn Thr Lys Tyr Asn Gly Asp Ser Asp Lys
            275                 280                 285

Ile Arg Gln Trp Val His Gln Ile Val Asn Thr Ile Asn Glu Ile Tyr
            290                 295                 300

Arg Pro Leu Asn Ile Gln Phe Thr Leu Val Gly Leu Glu Ile Trp Ser
305                 310                 315                 320

Asn Gln Asp Leu Ile Thr Val Thr Ser Val Ser His Asp Thr Leu Ala
                325                 330                 335

Ser Phe Gly Asn Trp Arg Glu Thr Asp Leu Leu Arg Arg Gln Arg His
            340                 345                 350

Asp Asn Ala Gln Leu Leu Thr Ala Ile Asp Phe Asp Gly Asp Thr Val
            355                 360                 365

Gly Leu Ala Tyr Val Gly Gly Met Cys Gln Leu Lys His Ser Thr Gly
            370                 375                 380

Val Ile Gln Asp His Ser Ala Ile Asn Leu Leu Val Ala Leu Thr Met
385                 390                 395                 400

Ala His Glu Leu Gly His Asn Leu Gly Met Asn His Asp Gly Asn Gln
                405                 410                 415

Cys His Cys Gly Ala Asn Ser Cys Val Met Ala Ala Met Leu Ser Asp
            420                 425                 430

Gln Pro Ser Lys Leu Phe Ser Asp Cys Ser Lys Lys Asp Tyr Gln Thr
            435                 440                 445

Phe Leu Thr Val Asn Asn Pro Gln Cys Ile Leu Asn Lys Pro
            450                 455                 460

<210> SEQ ID NO 4
<211> LENGTH: 1386
<212> TYPE: DNA
<213> ORGANISM: Artificial
<220> FEATURE:
<223> OTHER INFORMATION: Encodes pro-NAT (analog of fibrolase)

<400> SEQUENCE: 4
atgagatttc cttcaatttt tactgctgtt ttattcgcag catcctccgc attagctgct      60
ccagtcaaca ctacaacaga agatgaaacg gcacaaattc cggctgaagc tgtcatcggt     120
tactcagatt tagaagggga tttcgatgtt gctgttttgc cattttccaa cagcacaaat     180
aacgggttat tgtttataaa tactactatt gccagcattg ctgctaaaga agaagggta      240 tctctcgaga aaagagaggc tgaagcttct tctattatct tggaatctgg taacgttaac     300
gattacgaag ttgtttatcc aagaaaggtc actccagttc ctaggggtgc tgttcaacca     360
```

-continued

```
aagtacgaag atgccatgca atacgaattc aaggttaaca gtgaaccagt tgtcttgcac    420
ttggaaaaaa acaaaggttt gttctctgaa gattactctg aaactcatta ctcccccagat   480 ggtagagaaa ttactactta cccattgggt gaagatcact gttactacca tggtagaatc    540
gaaaacgatg ctgactccac tgcttctatc tctgcttgta acggtttgaa gggtcatttc    600
aagttgcaag gtgaaatgta cttgattgaa ccattggaat tgtccgactc tgaagcccat    660
gctgtctaca gtacgaaaa cgtcgaaaag gaagatgaag ccccaaagat gtgtggtgtt     720
acccaaaact gggaatcata tgaaccaatc aagaaggcct ccaattaaa cttgactaag     780 agatctttcc cacaaagata cgtacagctg gttatcgttg ctgaccaccg tatgaacact    840
aaatacaacg gtgactctga caaatccgt caatgggtgc accaaatcgt caacaccatt     900
aacgaaatct acagaccact gaacatccaa ttcactttgg ttggtttgga aatctggtcc    960
aaccaagatt tgatcaccgt tacttctgta tcccacgaca ctctggcatc cttcggtaac    1020
tggcgtgaaa ccgacctgct gcgtcgccaa cgtcatgata acgctcaact gctgaccgct   1080
atcgacttcg acggtgatac tgttggtctg cttacgttg tggcatgtg tcaactgaaa     1140 cattctactg gtgttatcca ggaccactcc gctattaacc tgctggttgc tctgaccatg    1200
gcacacgaac tgggtcataa cctgggtatg aaccacgatg caaccagtg tcactgcggt    1260 gcaaactcct gtgttatggc tgctatgctg tccgatcaac catccaaact gttctccgac   1320
tgctctaaga aagactacca gaccttcctg accgttaaca cccgcagtg tatcctgaac    1380 aaaccg                                                              1386
```

<210> SEQ ID NO 5
<211> LENGTH: 203
<212> TYPE: PRT
<213> ORGANISM: Agkistrodon contortrix
<220> FEATURE:
<221> NAME/KEY: misc_feature
<223> OTHER INFORMATION: Native fibrolase of Agkistrodon contortrix

<400> SEQUENCE: 5

```
Gln Gln Arg Phe Pro Gln Arg Tyr Val Gln Leu Val Ile Val Ala Asp
1               5                   10                  15

His Arg Met Asn Thr Lys Tyr Asn Gly Asp Ser Asp Lys Ile Arg Gln
            20                  25                  30

Trp Val His Gln Ile Val Asn Thr Ile Asn Glu Ile Tyr Arg Pro Leu
        35                  40                  45

Asn Ile Gln Phe Thr Leu Val Gly Leu Glu Ile Trp Ser Asn Gln Asp
    50                  55                  60

Leu Ile Thr Val Thr Ser Val Ser His Asp Thr Leu Ala Ser Phe Gly
65                  70                  75                  80

Asn Trp Arg Glu Thr Asp Leu Leu Arg Arg Gln Arg His Asp Asn Ala
                85                  90                  95

Gln Leu Leu Thr Ala Ile Asp Phe Asp Gly Asp Thr Val Gly Leu Ala
            100                 105                 110

Tyr Val Gly Gly Met Cys Gln Leu Lys His Ser Thr Gly Val Ile Gln
        115                 120                 125

Asp His Ser Ala Ile Asn Leu Leu Val Ala Leu Thr Met Ala His Glu
    130                 135                 140

Leu Gly His Asn Leu Gly Met Asn His Asp Gly Asn Gln Cys His Cys
145                 150                 155                 160

Gly Ala Asn Ser Cys Val Met Ala Ala Met Leu Ser Asp Gln Pro Ser
```

-continued

```
            165                 170                 175

Lys Leu Phe Ser Asp Cys Ser Lys Lys Asp Tyr Gln Thr Phe Leu Thr
        180                 185                 190

Val Asn Asn Pro Gln Cys Ile Leu Asn Lys Pro
    195                 200

<210> SEQ ID NO 6
<211> LENGTH: 609
<212> TYPE: DNA
<213> ORGANISM: Agkistrodon contortrix

<400> SEQUENCE: 6
caacaaagat tcccacaaag atacgtacag ctggttatcg ttgctgacca ccgtatgaac      60
actaaataca acggtgactc tgacaaaatc cgtcaatggg tgcaccaaat cgtcaacacc     120
attaacgaaa tctacagacc actgaacatc caattcactt tggttggttt ggaaatctgg     180
tccaaccaag atttgatcac cgttacttct gtatcccacg acactctggc atccttcggt     240
aactggcgtg aaaccgacct gctgcgtcgc caacgtcatg ataacgctca actgctgacc     300
gctatcgact tcgacggtga tactgttggt ctggcttacg ttggtggcat gtgtcaactg     360
aaacattcta ctggtgttat ccaggaccac tccgctatta acctgctggt tgctctgacc     420
atggcacacg aactgggtca taacctgggt atgaaccacg atggcaacca gtgtcactgc     480
ggtgcaaact cctgtgttat ggctgctatg ctgtccgatc aaccatccaa actgttctcc     540
gactgctcta agaaagacta ccagaccttc ctgaccgtta acaacccgca gtgtatcctg     600
aacaaaccg                                                             609

<210> SEQ ID NO 7
<211> LENGTH: 1392
<212> TYPE: DNA
<213> ORGANISM: Agkistrodon contortrix

<400> SEQUENCE: 7
atgagatttc cttcaatttt tactgctgtt ttattcgcag catcctccgc attagctgct      60
ccagtcaaca ctacaacaga agatgaaacg gcacaaattc cggctgaagc tgtcatcggt     120
tactcagatt tagaagggga tttcgatgtt gctgttttgc cattttccaa cagcacaaat     180
aacgggttat tgtttataaa tactactatt gccagcattg ctgctaaaga agaaggggta     240
tctctcgaga aaagagaggc tgaagcttct tctattatct tggaatctgg taacgttaac     300
gattacgaag ttgtttatcc aagaaaggtc actccagttc ctaggggtgc tgttcaacca     360
aagtacgaag atgccatgca atacgaattc aaggttaaca gtgaaccagt tgtcttgcac     420
ttggaaaaaa acaaaggttt gttctctgaa gattactctg aaactcatta ctccccagat     480
ggtagagaaa ttactactta cccattgggt gaagatcact gttactacca tggtagaatc     540
gaaaacgatg ctgactccac tgcttctatc tctgcttgta acggtttgaa gggtcatttc     600
aagttgcaag gtgaaatgta cttgattgaa ccattggaat tgtccgactc tgaagcccat     660
gctgtctaca agtacgaaaa cgtcgaaaag gaagatgaag ccccaaagat gtgtggtgtt     720
acccaaaact gggaatcata tgaaccaatc aagaaggcct tccaattaaa cttgactaag     780
agacaacaaa gattcccaca aagatacgta cagctggtta tcgttgctga ccaccgtatg     840
aacactaaat acaacggtga ctctgacaaa atccgtcaat gggtgcacca aatcgtcaac     900
accattaacg aaatctacag accactgaac atccaattca ctttggttgg tttggaaatc     960
tggtccaacc aagatttgat caccgttact tctgtatccc acgacactct ggcatccttc    1020
```

```
ggtaactggc gtgaaaccga cctgctgcgt cgccaacgtc atgataacgc tcaactgctg      1080
accgctatcg acttcgacgg tgatactgtt ggtctggctt acgttggtgg catgtgtcaa      1140
ctgaaacatt ctactggtgt tatccaggac cactccgcta ttaacctgct ggttgctctg      1200
accatggcac acgaactggg tcataacctg ggtatgaacc acgatggcaa ccagtgtcac      1260
tgcggtgcaa actcctgtgt tatggctgct atgctgtccg atcaaccatc caaactgttc      1320
tccgactgct ctaagaaaga ctaccagacc ttcctgaccg ttaacaaccc gcagtgtatc      1380
ctgaacaaac cg                                                         1392
```

<210> SEQ ID NO 8
<211> LENGTH: 21
<212> TYPE: DNA
<213> ORGANISM: Artificial
<220> FEATURE:
<223> OTHER INFORMATION: Oligonucleotide

<400> SEQUENCE: 8

```
tactattgcc agcattgctg c                                                21
```

<210> SEQ ID NO 9
<211> LENGTH: 21
<212> TYPE: DNA
<213> ORGANISM: Artificial
<220> FEATURE:
<223> OTHER INFORMATION: Oligonucleotide

<400> SEQUENCE: 9

```
gcaaatggca ttctgacatc c                                                21
```

<210> SEQ ID NO 10
<211> LENGTH: 45
<212> TYPE: DNA
<213> ORGANISM: Artificial
<220> FEATURE:
<223> OTHER INFORMATION: Oligonucleotide

<400> SEQUENCE: 10

```
tccaattaaa cttgactaag agatctttcc cacaaagata cgtac                      45
```

<210> SEQ ID NO 11
<211> LENGTH: 44
<212> TYPE: DNA
<213> ORGANISM: Artificial
<220> FEATURE:
<223> OTHER INFORMATION: Oligonucleotide

<400> SEQUENCE: 11

```
gtacgtatct ttgtgggaaa gatctcttag tcaagtttaa ttgg                       44
```

<210> SEQ ID NO 12
<211> LENGTH: 1620
<212> TYPE: DNA
<213> ORGANISM: Agkistrodon contortrix
<220> FEATURE:
<221> NAME/KEY: misc_feature
<222> LOCATION: (1)..(1620)
<223> OTHER INFORMATION: Complementary (sense) strand of antisense
      strand (See SEQ ID NO:13
<221> NAME/KEY: misc_feature
<223> OTHER INFORMATION: Coding sequence of native pro-fibrolase of
      Agkistrodon contortrix

<400> SEQUENCE: 12

-continued

```
atgagatttc cttcaatttt tactgctgtt ttattcgcag catcctccgc attagctgct    60
ccagtcaaca ctacaacaga agatgaaacg gcacaaattc cggctgaagc tgtcatcggt   120
tactcagatt tagaagggga tttcgatgtt gctgttttgc cattttccaa cagcacaaat   180
aacgggttat tgtttataaa tactactatt gccagcattg ctgctaaaga agaagggta    240 tctctcgaga aaagagaggc tgaagcttct tctattatct tggaatctgg taacgttaac   300
gattacgaag ttgtttatcc aagaaaggtc actccagttc ctagggtgc tgttcaacca    360 aagtacgaag atgccatgca atacgaattc aaggttaaca gtgaaccagt tgtcttgcac   420
ttggaaaaaa acaaaggttt gttctctgaa gattactctg aaactcatta ctccccagat   480
ggtagagaaa ttactactta cccattgggt gaagatcact gttactacca tggtagaatc   540
gaaaacgatg ctgactccac tgcttctatc tctgcttgta acggtttgaa gggtcatttc   600
aagttgcaag gtgaaatgta cttgattgaa ccattggaat tgtccgactc tgaagcccat   660
gctgtctaca agtacgaaaa cgtcgaaaag gaagatgaag ccccaaagat gtgtggtgtt   720
acccaaaact gggaatcata tgaaccaatc aagaaggcct tccaattaaa cttgactaag   780
agacaacaaa gattcccaca agatacgta cagctggtta tcgttgctga ccaccgtatg    840
aacactaaat acaacggtga ctctgacaaa atccgtcaat gggtgcacca aatcgtcaac   900
accattaacg aaatctacag accactgaac atccaattca ctttggttgg tttggaaatc   960
tggtccaacc aagatttgat caccgttact tctgtatccc acgacactct ggcatccttc  1020
ggtaactggc gtgaaaccga cctgctgcgt cgccaacgtc atgataacgc tcaactgctg  1080
accgctatcg acttcgacgg tgatactgtt ggtctggctt acgttggtgg catgtgtcaa  1140
ctgaaacatt ctactggtgt tatccaggac cactccgcta ttaacctgct ggttgctctg  1200
accatggcac acgaactggg tcataacctg ggtatgaacc acgatggcaa ccagtgtcac  1260
tgcggtgcaa actcctgtgt tatggctgct atgctgtccg atcaaccatc caaactgttc  1320
tccgactgct ctaagaaaga ctaccagacc ttcctgaccg ttaacaaccc gcagtgtatc  1380
ctgaacaaac cgtaagcggc cgccagcttt ctagaacaaa aactcatctc agaagaggat  1440
ctgaatagcg ccgtcgacca tcatcatcat catcattgag tttgtagcct tagacatgac  1500
tgttcctcag ttcaagttgg gcacttacga gaagaccggt cttgctagat tctaatcaag  1560
aggatgtcag aatgccattt gcctgagaga tgcaggcttc atttttgata ctttttatt   1620
```

<210> SEQ ID NO 13
<211> LENGTH: 1620
<212> TYPE: DNA
<213> ORGANISM: Agkistrodon contortrix
<220> FEATURE:
<221> NAME/KEY: misc_feature
<222> LOCATION: (1)..(1620)
<223> OTHER INFORMATION: Complementary (antisense) strand of sense
      strand (See SEQ ID NO:12
<221> NAME/KEY: misc_feature
<223> OTHER INFORMATION: Anti-coding sequence of native pro-fibrolase of
      Agkistrodon contortri

<400> SEQUENCE: 13

```
aataaaaaag tatcaaaaat gaagcctgca tctctcaggc aaatggcatt ctgacatcct     60
cttgattaga atctagcaag accggtcttc tcgtaagtgc ccaacttgaa ctgaggaaca    120
gtcatgtcta aggctacaaa ctcaatgatg atgatgatga tggtcgacgg cgctattcag    180
atcctcttct gagatgagtt tttgttctag aaagctggcg gccgcttacg gtttgttcag    240
gatacactgc gggttgttaa cggtcaggaa ggtctggtag tctttcttag agcagtcgga    300
```

```
gaacagtttg gatggttgat cggacagcat agcagccata acacaggagt ttgcaccgca    360
gtgacactgg ttgccatcgt ggttcatacc caggttatga cccagttcgt gtgccatggt    420
cagagcaacc agcaggttaa tagcggagtg gtcctggata acaccagtag aatgtttcag    480
ttgacacatg ccaccaacgt aagccagacc aacagtatca ccgtcgaagt cgatagcgtt    540
cagcagttga gcgttatcat gacgttggcg acgcagcagg tcggtttcac gccagttacc    600
gaaggatgcc agagtgtcgt gggatacaga agtaacggtg atcaaatctt ggttggacca    660
gatttccaaa ccaaccaaag tgaattggat gttcagtggc tgtagatttt cgttaatggt    720
gttgacgatt tggtgcaccc attgacggat tttgtcagag tcaccgttgt atttagtgtt    780
catacggtgg tcagcaacga taaccagctg tacgtatctt tgtgggaatc tttgttgtct    840
cttagtcaag tttaattgga aggccttctt gattggttca tatgattccc agttttgggt    900
aacaccacac atctttgggg cttcatcttc cttttcgacg ttttcgtact gtagacagc     960 atgggcttca gagtcggaca attccaatgg ttcaatcaag tacatttcac cttgcaactt    1020
gaaatgaccc ttcaaaccgt tacaagcaga gatagaagca gtggagtcag catcgttttc    1080
gattctacca tggtagtaac agtgatcttc acccaatggg taagtagtaa tttctctacc    1140
atctggggag taatgagttt cagagtaatc ttcagagaac aaaccttttgt tttttttccaa   1200 gtgcaagaca actggttcac tgttaacctt gaattcgtat tgcatggcat cttcgtactt    1260
tggttgaaca gcaccectag gaactggagt gacctttctt ggataaacaa cttcgtaatc    1320
gttaacgtta ccagattcca agataataga agaagcttca gcctctcttt tctcgagaga    1380
taccccttct tctttagcag caatgctggc aatagtagta tttataaaca ataacccgtt    1440
atttgtgctg ttggaaaatg gcaaaacagc aacatcgaaa tccccttcta aatctgagta    1500
accgatgaca gcttcagccg gaatttgtgc cgtttcatct tctgttgtag tgttgactgg    1560
agcagctaat gcggaggatg ctgcgaataa aacagcagta aaaattgaag gaaatctcat    1620
```

<210> SEQ ID NO 14
<211> LENGTH: 464
<212> TYPE: PRT
<213> ORGANISM: Agkistrodon contortrix
<220> FEATURE:
<221> NAME/KEY: misc_feature
<223> OTHER INFORMATION: Native pro-fibrolase of Agkistrodon contortrix

<400> SEQUENCE: 14

Met Arg Phe Pro Ser Ile Phe Thr Ala Val Leu Phe Ala Ala Ser Ser
1 5 10 15

Ala Leu Ala Ala Pro Val Asn Thr Thr Thr Glu Asp Glu Thr Ala Gln
20 25 30

Ile Pro Ala Glu Ala Val Ile Gly Tyr Ser Asp Leu Glu Gly Asp Phe
35 40 45

Asp Val Ala Val Leu Pro Phe Ser Asn Ser Thr Asn Asn Gly Leu Leu
50 55 60

Phe Ile Asn Thr Thr Ile Ala Ser Ile Ala Ala Lys Glu Glu Gly Val
65 70 75 80

Ser Leu Glu Lys Arg Glu Ala Glu Ala Ser Ser Ile Ile Leu Glu Ser
85 90 95

Gly Asn Val Asn Asp Tyr Glu Val Val Tyr Pro Arg Lys Val Thr Pro
100 105 110

Val Pro Arg Gly Ala Val Gln Pro Lys Tyr Glu Asp Ala Met Gln Tyr
115 120 125

```
Glu Phe Lys Val Asn Ser Glu Pro Val Val Leu His Leu Glu Lys Asn
    130                 135                 140

Lys Gly Leu Phe Ser Glu Asp Tyr Ser Glu Thr His Tyr Ser Pro Asp
145                 150                 155                 160

Gly Arg Glu Ile Thr Thr Tyr Pro Leu Gly Glu Asp His Cys Tyr Tyr
                165                 170                 175

His Gly Arg Ile Glu Asn Asp Ala Asp Ser Thr Ala Ser Ile Ser Ala
            180                 185                 190

Cys Asn Gly Leu Lys Gly His Phe Lys Leu Gln Gly Glu Met Tyr Leu
        195                 200                 205

Ile Glu Pro Leu Glu Leu Ser Asp Ser Glu Ala His Ala Val Tyr Lys
    210                 215                 220

Tyr Glu Asn Val Glu Lys Glu Asp Glu Ala Pro Lys Met Cys Gly Val
225                 230                 235                 240

Thr Gln Asn Trp Glu Ser Tyr Glu Pro Ile Lys Lys Ala Phe Gln Leu
                245                 250                 255

Asn Leu Thr Lys Arg Gln Gln Arg Phe Pro Gln Arg Tyr Val Gln Leu
            260                 265                 270

Val Ile Val Ala Asp His Arg Met Asn Thr Lys Tyr Asn Gly Asp Ser
        275                 280                 285

Asp Lys Ile Arg Gln Trp Val His Gln Ile Val Asn Thr Ile Asn Glu
    290                 295                 300

Ile Tyr Arg Pro Leu Asn Ile Gln Phe Thr Leu Val Gly Leu Glu Ile
305                 310                 315                 320

Trp Ser Asn Gln Asp Leu Ile Thr Val Thr Ser Val Ser His Asp Thr
                325                 330                 335

Leu Ala Ser Phe Gly Asn Trp Arg Glu Thr Asp Leu Leu Arg Arg Gln
            340                 345                 350

Arg His Asp Asn Ala Gln Leu Leu Thr Ala Ile Asp Phe Asp Gly Asp
        355                 360                 365

Thr Val Gly Leu Ala Tyr Val Gly Gly Met Cys Gln Leu Lys His Ser
    370                 375                 380

Thr Gly Val Ile Gln Asp His Ser Ala Ile Asn Leu Leu Val Ala Leu
385                 390                 395                 400

Thr Met Ala His Glu Leu Gly His Asn Leu Gly Met Asn His Asp Gly
                405                 410                 415

Asn Gln Cys His Cys Gly Ala Asn Ser Cys Val Met Ala Ala Met Leu
            420                 425                 430

Ser Asp Gln Pro Ser Lys Leu Phe Ser Asp Cys Ser Lys Lys Asp Tyr
        435                 440                 445

Gln Thr Phe Leu Thr Val Asn Asn Pro Gln Cys Ile Leu Asn Lys Pro
    450                 455                 460
```

<210> SEQ ID NO 15
<211> LENGTH: 203
<212> TYPE: PRT
<213> ORGANISM: Agkistrodon contortrix
<220> FEATURE:
<221> NAME/KEY: misc_feature
<223> OTHER INFORMATION: Native fibrolase of Agkistrodon contortrix
<221> NAME/KEY: misc_feature
<223> OTHER INFORMATION: Xaa in position 1 represents the chemical
      compound, pyroglutamic acid. This chemical compound is
      referred to in the specification as the letter "E"

<400> SEQUENCE: 15

```
Xaa Gln Arg Phe Pro Gln Arg Tyr Val Gln Leu Val Ile Val Ala Asp
1               5                   10                  15

His Arg Met Asn Thr Lys Tyr Asn Gly Asp Ser Asp Lys Ile Arg Gln
            20                  25                  30

Trp Val His Gln Ile Val Asn Thr Ile Asn Glu Ile Tyr Arg Pro Leu
            35                  40                  45

Asn Ile Gln Phe Thr Leu Val Gly Leu Glu Ile Trp Ser Asn Gln Asp
        50                  55                  60

Leu Ile Thr Val Thr Ser Val Ser His Asp Thr Leu Ala Ser Phe Gly
65                  70                  75                  80

Asn Trp Arg Glu Thr Asp Leu Leu Arg Arg Gln Arg His Asp Asn Ala
                85                  90                  95

Gln Leu Leu Thr Ala Ile Asp Phe Asp Gly Asp Thr Val Gly Leu Ala
                100                 105                 110

Tyr Val Gly Gly Met Cys Gln Leu Lys His Ser Thr Gly Val Ile Gln
            115                 120                 125

Asp His Ser Ala Ile Asn Leu Leu Val Ala Leu Thr Met Ala His Glu
130                 135                 140

Leu Gly His Asn Leu Gly Met Asn His Asp Gly Asn Gln Cys His Cys
145                 150                 155                 160

Gly Ala Asn Ser Cys Val Met Ala Ala Met Leu Ser Asp Gln Pro Ser
                165                 170                 175

Lys Leu Phe Ser Asp Cys Ser Lys Lys Asp Tyr Gln Thr Phe Leu Thr
                180                 185                 190

Val Asn Asn Pro Gln Cys Ile Leu Asn Lys Pro
            195                 200

<210> SEQ ID NO 16
<211> LENGTH: 202
<212> TYPE: PRT
<213> ORGANISM: Agkistrodon contortrix
<220> FEATURE:
<221> NAME/KEY: misc_feature
<223> OTHER INFORMATION: Native fibrolase of Agkistrodon contortrix
<221> NAME/KEY: misc_feature
<223> OTHER INFORMATION: Xaa in position 1 represents the chemical
      compound, pyroglutamic acid. This chemical compound is
      referred to in the specification as the letter "E"

<400> SEQUENCE: 16

Xaa Arg Phe Pro Gln Arg Tyr Val Gln Leu Val Ile Val Ala Asp His
1               5                   10                  15

Arg Met Asn Thr Lys Tyr Asn Gly Asp Ser Asp Lys Ile Arg Gln Trp
            20                  25                  30

Val His Gln Ile Val Asn Thr Ile Asn Glu Ile Tyr Arg Pro Leu Asn
            35                  40                  45

Ile Gln Phe Thr Leu Val Gly Leu Glu Ile Trp Ser Asn Gln Asp Leu
        50                  55                  60

Ile Thr Val Thr Ser Val Ser His Asp Thr Leu Ala Ser Phe Gly Asn
65                  70                  75                  80

Trp Arg Glu Thr Asp Leu Leu Arg Arg Gln Arg His Asp Asn Ala Gln
                85                  90                  95

Leu Leu Thr Ala Ile Asp Phe Asp Gly Asp Thr Val Gly Leu Ala Tyr
                100                 105                 110

Val Gly Gly Met Cys Gln Leu Lys His Ser Thr Gly Val Ile Gln Asp
            115                 120                 125

His Ser Ala Ile Asn Leu Leu Val Ala Leu Thr Met Ala His Glu Leu
```

```
                    130                 135                 140
Gly His Asn Leu Gly Met Asn His Asp Gly Asn Gln Cys His Cys Gly
145                 150                 155                 160

Ala Asn Ser Cys Val Met Ala Ala Met Leu Ser Asp Gln Pro Ser Lys
                165                 170                 175

Leu Phe Ser Asp Cys Ser Lys Lys Asp Tyr Gln Thr Phe Leu Thr Val
                180                 185                 190

Asn Asn Pro Gln Cys Ile Leu Asn Lys Pro
                195                 200

<210> SEQ ID NO 17
<211> LENGTH: 462
<212> TYPE: PRT
<213> ORGANISM: Artificial
<220> FEATURE:
<223> OTHER INFORMATION: Analog form of native pro-fibrolase of
      Agkistrodon contortrix

<400> SEQUENCE: 17

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Ser Asp Leu Glu Gly Asp Phe
            35                  40                  45

Asp Val Ala Val Leu Pro Phe Ser Asn Ser Thr Asn Asn Gly Leu Leu
        50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Ser Ser Ile Ile Leu Glu Ser
                85                  90                  95

Gly Asn Val Asn Asp Tyr Glu Val Val Tyr Pro Arg Lys Val Thr Pro
                100                 105                 110

Val Pro Arg Gly Ala Val Gln Pro Lys Tyr Glu Asp Ala Met Gln Tyr
            115                 120                 125

Glu Phe Lys Val Asn Ser Glu Pro Val Val Leu His Leu Glu Lys Asn
130                 135                 140

Lys Gly Leu Phe Ser Glu Asp Tyr Ser Glu Thr His Tyr Ser Pro Asp
145                 150                 155                 160

Gly Arg Glu Ile Thr Thr Tyr Pro Leu Gly Glu Asp His Cys Tyr Tyr
                165                 170                 175

His Gly Arg Ile Glu Asn Asp Ala Asp Ser Thr Ala Ser Ile Ser Ala
                180                 185                 190

Cys Asn Gly Leu Lys Gly His Phe Lys Leu Gln Gly Glu Met Tyr Leu
                195                 200                 205

Ile Glu Pro Leu Glu Leu Ser Asp Ser Glu Ala His Ala Val Tyr Lys
            210                 215                 220

Tyr Glu Asn Val Glu Lys Glu Asp Glu Ala Pro Lys Met Cys Gly Val
225                 230                 235                 240

Thr Gln Asn Trp Glu Ser Tyr Glu Pro Ile Lys Lys Ala Phe Gln Leu
                245                 250                 255

Asn Leu Thr Lys Arg Ser Phe Pro Gln Arg Tyr Val Gln Leu Val Ile
                260                 265                 270

Val Ala Asp His Arg Met Asn Thr Lys Tyr Asn Gly Asp Ser Asp Lys
            275                 280                 285
```

```
Ile Arg Gln Trp Val His Gln Ile Val Asn Thr Ile Asn Glu Ile Tyr
    290                 295                 300
Arg Pro Leu Asn Ile Gln Phe Thr Leu Val Gly Leu Glu Ile Trp Ser
305                 310                 315                 320
Asn Gln Asp Leu Ile Thr Val Thr Ser Val Ser His Asp Thr Leu Ala
                325                 330                 335
Ser Phe Gly Asn Trp Arg Glu Thr Asp Leu Leu Arg Arg Gln Arg His
            340                 345                 350
Asp Asn Ala Gln Leu Leu Thr Ala Ile Asp Phe Asp Gly Asp Thr Val
        355                 360                 365
Gly Leu Ala Tyr Val Gly Gly Met Cys Gln Leu Lys His Ser Thr Gly
    370                 375                 380
Val Ile Gln Asp His Ser Ala Ile Asn Leu Leu Val Ala Leu Thr Met
385                 390                 395                 400
Ala His Glu Leu Gly His Asn Leu Gly Met Asn His Asp Gly Asn Gln
                405                 410                 415
Cys His Cys Gly Ala Asn Ser Cys Val Met Ala Ala Met Leu Ser Asp
            420                 425                 430
Gln Pro Ser Lys Leu Phe Ser Asp Cys Ser Lys Lys Asp Tyr Gln Thr
        435                 440                 445
Phe Leu Thr Val Asn Asn Pro Gln Cys Ile Leu Asn Lys Pro
    450                 455                 460

<210> SEQ ID NO 18
<211> LENGTH: 602
<212> TYPE: DNA
<213> ORGANISM: Agkistrodon contortrix
<220> FEATURE:
<221> NAME/KEY: misc_feature
<223> OTHER INFORMATION: Fragment of fibrolase of Agkistrodon contortrix

<400> SEQUENCE: 18
tactattgcc agcattgctg ctaaagaaga agggtatct ctcgagaaaa gagaggctga      60
agcttcttct attatcttgg aatctggtaa cgttaacgat tacgaagttg tttatccaag    120
aaaggtcact ccagttccta ggggtgctgt tcaaccaaag tacgaagatg ccatgcaata    180
cgaattcaag gttaacagtg aaccagttgt cttgcacttg gaaaaaaaca aaggtttgtt    240
ctctgaagat tactctgaaa ctcattactc cccagatggt agagaaatta ctacttaccc    300
attgggtgaa gatcactgtt actaccatgg tagaatcgaa aacgatgctg actccactgc    360
ttctatctct gcttgtaacg gtttgaaggg tcatttcaag ttgcaaggtg aaatgtactt    420
gattgaacca ttggaattgt ccgactctga agcccatgct gtctacaagt acgaaaacgt    480
cgaaaaggaa gatgaagccc aaagatgtg tggtgttacc caaaactggg aatcatatga    540
accaatcaag aaggccttcc aattaaactt gactaagaga tctttcccac aaagatacgt    600
ac                                                                    602

<210> SEQ ID NO 19
<211> LENGTH: 816
<212> TYPE: DNA
<213> ORGANISM: Agkistrodon contortrix
<220> FEATURE:
<221> NAME/KEY: misc_feature
<223> OTHER INFORMATION: Fragment of fibrolase of Agkistrodon contortrix

<400> SEQUENCE: 19
tccaattaaa cttgactaag agatctttcc cacaaagata cgtacagctg gttatcgttg     60
```

-continued

```
ctgaccaccg tatgaacact aaatacaacg gtgactctga caaaatccgt caatgggtgc      120
accaaatcgt caacaccatt aacgaaatct acagaccact gaacatccaa ttcactttgg      180 ttggttttgga atctggtcc aaccaagatt tgatcaccgt tacttctgta tcccacgaca      240
ctctggcatc cttcggtaac tggcgtgaaa ccgacctgct gcgtcgccaa cgtcatgata      300
acgctcaact gctgaccgct atcgacttcg acggtgatac tgttggtctg gcttacgttg      360
gtggcatgtg tcaactgaaa cattctactg gtgttatcca ggaccactcc gctattaacc      420
tgctggttgc tctgaccatg gcacacgaac tgggtcataa cctgggtatg aaccacgatg      480
gcaaccagtg tcactgcggt gcaaactcct gtgttatggc tgctatgctg tccgatcaac      540
catccaaact gttctccgac tgctctaaga aagactacca gaccttcctg accgttaaca      600
acccgcagtg tatcctgaac aaaccgtaag cggccgccag ctttctagaa caaaaactca      660
tctcagaaga ggatctgaat agcgccgtcg accatcatca tcatcatcat tgagtttgta      720
gccttagaca tgactgttcc tcagttcaag ttgggcactt acgagaagac cggtcttgct      780
agattctaat caagaggatg tcagaatgcc atttgc                                816
```

<210> SEQ ID NO 20
<211> LENGTH: 1373
<212> TYPE: DNA
<213> ORGANISM: Agkistrodon contortrix
<220> FEATURE:
<221> NAME/KEY: misc_feature
<223> OTHER INFORMATION: Fragment of fibrolase of Agkistrodon contortrix
<400> SEQUENCE: 20

```
tactattgcc agcattgctg ctaaagaaga agggtatct ctcgagaaaa gagaggctga       60
agcttcttct attatcttgg aatctggtaa cgttaacgat tacgaagttg tttatccaag      120
aaaggtcact ccagttccta ggggtgctgt caaccaaag tacgaagatg ccatgcaata      180
cgaattcaag gttaacagtg aaccagttgt cttgcacttg gaaaaaaaca aaggtttgtt      240
ctctgaagat tactctgaaa ctcattactc cccagatggt agagaaatta ctacttaccc      300
attgggtgaa gatcactgtt actaccatgg tagaatcgaa acgatgctg actccactgc      360 ttctatctct gcttgtaacg gtttgaaggg tcatttcaag ttgcaaggtg aaatgtactt      420
gattgaacca ttggaattgt ccgactctga agcccatgct gtctacaagt acgaaaacgt      480
cgaaaaggaa gatgaagccc caagatgtg tggtgttacc caaaactggg aatcatatga      540
accaatcaag aaggccttcc aattaaactt gactaagaga tctttcccac aaagatacgt      600
acagctggtt atcgttgctg accaccgtat gaacactaaa tacaacggtg actctgacaa      660
aatccgtcaa tgggtgcacc aaatcgtcaa caccattaac gaaatctaca gaccactgaa      720
catccaattc actttggttg gtttggaaat ctggtccaac caagatttga tcaccgttac      780
ttctgtatcc cacgacactc tggcatcctt cggtaactgg cgtgaaaccg acctgctgcg      840
tcgccaacgt catgataacg ctcaactgct gaccgctatc gacttcgacg gtgatactgt      900
tggtctggct tacgttggtg gcatgtgtca actgaaacat tctactggtg ttatccagga      960
ccactccgct attaacctgc tggttgctct gaccatggca cacgaactgg gtcataacct     1020
gggtatgaac cacgatggca accagtgtca ctgcggtgca aactcctgtg ttatggctgc     1080
tatgctgtcc gatcaaccat ccaaactgtt ctccgactgc tctaagaaag actaccagac     1140
cttcctgacc gttaacaacc cgcagtgtat cctgaacaaa ccgtaagcgg ccgccagctt     1200
tctagaacaa aaactcatct cagaagagga tctgaatagc gccgtcgacc atcatcatca     1260
```

```
tcatcattga gtttgtagcc ttagacatga ctgttcctca gttcaagttg ggcacttacg   1320
agaagaccgg tcttgctaga ttctaatcaa gaggatgtca gaatgccatt tgc          1373
```

<210> SEQ ID NO 21
<211> LENGTH: 4
<212> TYPE: PRT
<213> ORGANISM: Artificial
<220> FEATURE:
<223> OTHER INFORMATION: Analog form of native pro-fibrolase of
      Agkistrodon contortrix

<400> SEQUENCE: 21

Lys Arg Arg Phe
1

<210> SEQ ID NO 22
<211> LENGTH: 27
<212> TYPE: PRT
<213> ORGANISM: Agkistrodon contortrix
<220> FEATURE:
<221> NAME/KEY: misc_feature
<223> OTHER INFORMATION: Native pro-fibrolase of Agkistrodon contortrix

<400> SEQUENCE: 22

Ala Ala Ala Ser Phe Leu Glu Gln Lys Leu Ile Ser Glu Glu Asp Leu
1               5                   10                  15

Asn Ser Ala Val Asp His His His His His His
            20                  25

<210> SEQ ID NO 23
<211> LENGTH: 22
<212> TYPE: PRT
<213> ORGANISM: Agkistrodon contortrix
<220> FEATURE:
<221> NAME/KEY: misc_feature
<223> OTHER INFORMATION: Native pro-fibrolase of Agkistrodon contortrix

<400> SEQUENCE: 23

Val Cys Ser Leu Arg His Asp Cys Ser Ser Val Gln Val Gly His Leu
1               5                   10                  15

Arg Glu Asp Arg Ser Cys
            20

<210> SEQ ID NO 24
<211> LENGTH: 19
<212> TYPE: PRT
<213> ORGANISM: Agkistrodon contortrix
<220> FEATURE:
<221> NAME/KEY: misc_feature
<223> OTHER INFORMATION: Native pro-fibrolase of Agkistrodon contortrix

<400> SEQUENCE: 24

Ile Leu Ile Lys Arg Met Ser Glu Cys His Leu Pro Glu Arg Cys Arg
1               5                   10                  15

Leu His Phe

<210> SEQ ID NO 25
<211> LENGTH: 4
<212> TYPE: PRT
<213> ORGANISM: Agkistrodon contortrix
<220> FEATURE:
<221> NAME/KEY: misc_feature
<223> OTHER INFORMATION: Native pro-fibrolase of Agkistrodon contortrix

<400> SEQUENCE: 25

```
Tyr Phe Phe Ile
1

<210> SEQ ID NO 26
<211> LENGTH: 27
<212> TYPE: PRT
<213> ORGANISM: Artificial
<220> FEATURE:
<223> OTHER INFORMATION: Analog form of native pro-fibrolase of
      Agkistrodon contortrix

<400> SEQUENCE: 26

Ala Ala Ala Ser Phe Leu Glu Gln Lys Leu Ile Ser Glu Glu Asp Leu
1               5                   10                  15

Asn Ser Ala Val Asp His His His His His His
            20                  25

<210> SEQ ID NO 27
<211> LENGTH: 22
<212> TYPE: PRT
<213> ORGANISM: Artificial
<220> FEATURE:
<223> OTHER INFORMATION: Analog form of native pro-fibrolase of
      Agkistrodon contortrix

<400> SEQUENCE: 27

Val Cys Ser Leu Arg His Asp Cys Ser Ser Val Gln Val Gly His Leu
1               5                   10                  15

Arg Glu Asp Arg Ser Cys
            20

<210> SEQ ID NO 28
<211> LENGTH: 19
<212> TYPE: PRT
<213> ORGANISM: Artificial
<220> FEATURE:
<223> OTHER INFORMATION: Analog form of native pro-fibrolase of
      Agkistrodon contortrix

<400> SEQUENCE: 28

Ile Leu Ile Lys Arg Met Ser Glu Cys His Leu Pro Glu Arg Cys Arg
1               5                   10                  15

Leu His Phe

<210> SEQ ID NO 29
<211> LENGTH: 4
<212> TYPE: PRT
<213> ORGANISM: Artificial
<220> FEATURE:
<223> OTHER INFORMATION: Analog form of native pro-fibrolase of
      Agkistrodon contortrix

<400> SEQUENCE: 29

Tyr Phe Phe Ile
```